United States Patent

Hamburg et al.

[11] Patent Number: 5,268,086
[45] Date of Patent: Dec. 7, 1993

[54] CATALYST MONITORING USING EGO SENSORS

[75] Inventors: Douglas R. Hamburg; Eleftherios M. Logothetis, both of Birmingham; Jacobus H. Visser, Belleville; Richard E. Soltis, Redford, all of Mich.

[73] Assignee: Ford Motor Company, Dearborn, Mich.

[21] Appl. No.: 741,378

[22] Filed: Aug. 7, 1991

[51] Int. Cl.$^5$ .................................. G01N 27/417
[52] U.S. Cl. ............................ 204/429; 204/424; 204/427
[58] Field of Search ............... 204/424, 426, 427, 428, 204/429

[56] References Cited

U.S. PATENT DOCUMENTS

| | | | |
|---|---|---|---|
| 3,962,866 | 6/1976 | Neidhard et al. | 60/276 |
| 3,969,932 | 7/1976 | Rieger et al. | 73/118 |
| 4,007,589 | 2/1977 | Neidhard et al. | 60/276 |
| 4,121,548 | 10/1978 | Hattori et al. | 123/32 EE |
| 4,528,086 | 7/1985 | Kato et al. | 204/427 |
| 4,622,809 | 11/1986 | Abthoff et al. | 60/274 |
| 4,626,337 | 12/1986 | Hotta et al. | 204/429 |
| 4,834,051 | 5/1989 | Tanaka et al. | 123/440 |
| 4,884,066 | 11/1989 | Miyata et al. | 340/633 |
| 4,990,235 | 2/1991 | Chujo | 204/424 |

OTHER PUBLICATIONS

SAE Paper #900062, "Detection of Catalyst Performance Loss Using on Board Diagnostics", Clemmens et al. U.S. Environmental Protection Agency.

Primary Examiner—John Niebling
Assistant Examiner—William T. Leader
Attorney, Agent, or Firm—Joseph W. Malleck; Roger L. May

[57] ABSTRACT

A method of monitoring, while on board an automotive vehicle, one or more of catalyst performance, engine misfire, and combustion quality, the vehicle having an internal combustion engine equipped with a catalyst for converting noxious emissions of the engine, comprising: (i) exposing at least one pair of EGO sensors to substantially the same emissions either exiting from the engine or from the catalyst, one of the EGO sensors having its electrode highly catalytic, and the other sensor having its electrode low-to-noncatalytic; (ii) comparing the outputs of the sensor electrodes (amplitude, frequency, or phase shift) to determine if there is a sufficient differential to indicate a misfire or poor combustion in the case of the sensors being located downstream of the engine exhaust but upstream of the catalyst, or indicating poor catalyst efficiency in the case of the sensors being placed substantially immediately downstream of the catalyst. The catalyst may be a three-way catalyst (or an oxidation catalyst). The sensors may be of the EGO, HEGO, or UEGO types. Two pairs of sensors may be used, a first pair being placed substantially immediately upstream of the catalyst and the second pair being placed substantially immediately downstream of the catalyst, the pairs of EGO sensors being incorporated into a closed-loop feedback control of the engine fuel control system.

5 Claims, 12 Drawing Sheets

EXPOSING DIFFERENTIALLY CATALYZED
ELECTRODES OF AN OXYGEN SENSING
SYSTEM TO EXHAUST GASES OF AN ENGINE
IN ESSENTIALLY THE SAME GASES,
EITHER UPSTREAM OR DOWNSTREAM
OF A MAIN CONVERSION CATALYST

↓

COMPARING THE SIGNAL OUTPUTS
FROM SUCH ELECTRODES FOR AN
INDICATION OF A SPECIFIC MALFUNCTION
WITH RESPECT EITHER TO ENGINE
MISFIRE, SLOW OR LATE BURN, OR
MAIN CATALYST DEGRADATION

Fig. 1

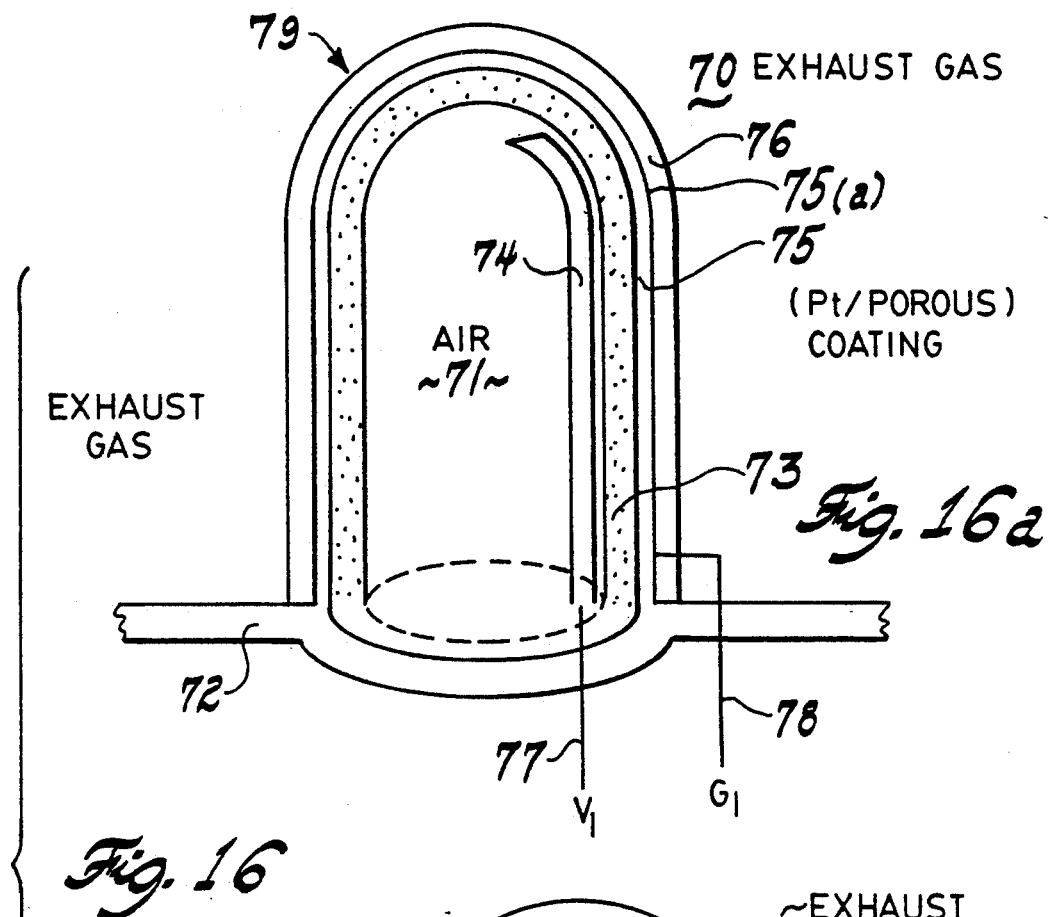
Fig. 16a
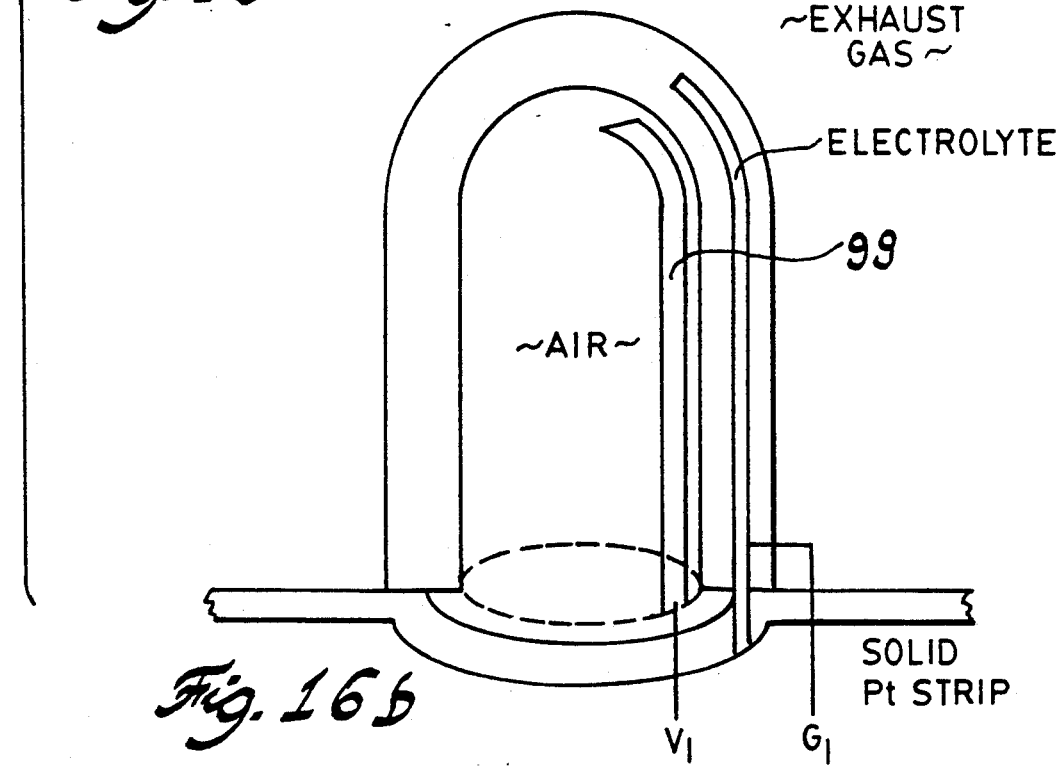
Fig. 16b
Fig. 16

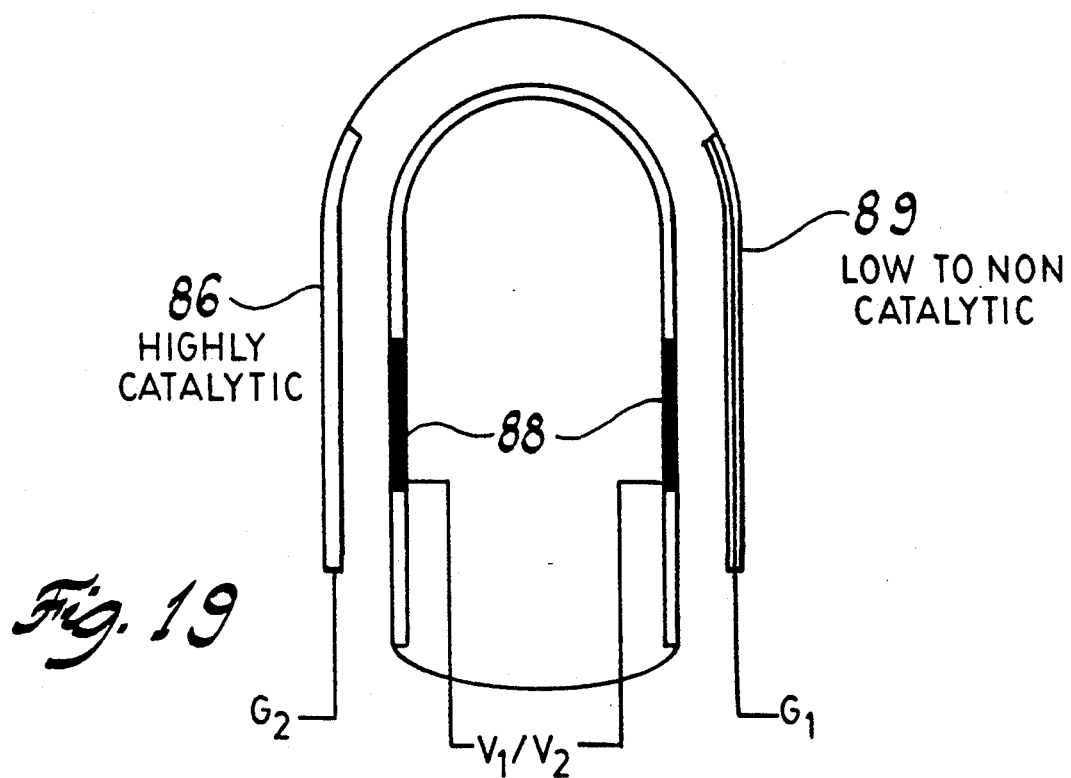

CATALYST MONITORING USING EGO SENSORS

BACKGROUND OF THE INVENTION

1. Technical Field

This invention relates to the art of using exhaust gas oxygen (EGO) sensors for detecting catalyst failure, such catalysts being of the type that converts automotive engine emissions to non-noxious gases and water vapor.

2. Discussion of the Prior Art

There is growing concern that to improve air quality in the United States, emission related components, such as a catalyst, must be monitored on board the vehicle to determine any malfunction. Catalyst monitoring has been and still is the least understood, both conceptually and practically, of the emission related components.

EGO sensors have been used in the past, in pairs, to monitor catalysts, one sensor being placed upstream from a catalyst and the other placed downstream of the catalyst, and the signals from each of such sensors were evaluated to determine any difference that would indicate the catalyst was degraded. It is presumed by such prior art that a properly operating catalyst would be capable of dampening the periodic rich to lean excursions resulting from the limit cycle A/F feedback control or intentionally generated in the exhaust stream and that a substantial loss in catalyst performance through loss in actual conversion activity and/or oxygen storage activity would result in a decrease in this dampening ability of the catalyst. This generalized approach to catalyst monitoring compares complex signal features from both devices, each of which is disposed in a different environment and exposed to different exhaust gas locations, and furthermore presumes that there is a correlation between catalyst oxygen storage sensed signal features, and catalyst performance. Often there is no such correlation. However, since each sensor uses a similar construction, including a catalytic coating that acts as a microcatalyst, failure based on the inability of the main catalyst to convert emissions may be hidden or masked by the sensor itself.

Patented variations of the two sensor catalyst monitoring system have utilized or compared many sensor signal characteristics, including voltage amplitude, phase shift, and frequency ratioing. In some cases, an artificial change in the sensor signal is created by modulation of the engine A/F ratio which, it is hoped, will more clearly show the onset of catalyst degradation. Unfortunately, all of such prior art approaches have at least the following characteristics in common: they expose the electrodes of the sensors to different emission gases, the sensors inherently have construction variations in tolerances and aging, and a decision as to catalyst degradation cannot be made without comparison to an artificial reference. Such prior art sensor system approaches are inaccurate not only due to such sensor differences but also are not able to sense a difference in oxygen between equilibrated and nonequilibrated oxygen conversion or combustion.

What is needed is a system that more reliably monitors catalyst degradation or inadequate engine combustion.

SUMMARY OF THE INVENTION

The invention uniquely deploys an EGO sensor's rapid ability to detect a gas mixture's difference from chemical equilibrium and not mask such ability by presuming the oxygen storage capability of a main catalyst must first be detected. This is a significant inversion of logic used by the prior art.

The invention herein uses an approach different than prior art to detect either catalyst malfunction or engine misfire. The invention recognizes that an engine or catalyst each are gas mixture equilibrators. That is, a properly functioning catalyst or engine burns combustible intake gases or fluids to near chemical equilibrium. However, a standard EGO sensor also is an equilibrator because it uses catalytic electrodes and coatings to more fully combust or "equilibrate" either engine or catalyst exhaust gases to improve its stoichiometric control point sensing accuracy. If the sensed gases are already at or near equilibrium, catalytic electrode or coatings activity would not be necessary and would perform no function; it would be superfluous.

The logic of this invention is based on controlled single factor variation. It follows below. Build nearly identical EGO sensor pairs which differ within a pair in that one sensor is fully catalytic while the other has reduced or no catalytic activity at its electrode or coating. Place such a nearly identical sensor pair in a common operating flow and gas environment downstream of either an engine or catalyst. If sensed gases are at or near equilibrium, there will not be a difference between the respective sensor outputs because a sensor's catalytic activity is not needed. If sensed gases are not at or near equilibrium (due to catalyst degradation or engine malfunction), there will be a difference between the sensors' outputs, because one sensor's catalytic activity is needed and is missing. The difference will occur because within a pair, one sensor's missing catalytic activity will actually be needed to bring gases to equilibrium.

Thus, the invention places differentially catalyzed electrodes of oxygen sensors in either the exhaust gas exiting from the engine or in the exhaust gas exiting from the catalyst, and then compares signals generated by each of the electrodes and, if a predetermined difference is present, makes indication, respectively, of engine malfunction or catalyst degradation. Monitoring, while on board an automotive vehicle, can be carried out for one or more of catalyst performance, engine misfire, and combustion quality, the vehicle having an internal combustion engine equipped with a catalyst for converting noxious emissions of the engine.

The catalyst may be a three-way catalyst or an oxidation catalyst. The sensors may be of the EGO, HEGO, or UEGO types. The sensors are used in pairs, a first pair being placed substantially immediately upstream of the catalyst and the second pair being placed substantially immediately downstream of the catalyst, the pairs of EGO sensors being incorporated into a closed-loop feedback control of the engine fuel control system. Both amplitude comparison, frequency change, or phase shift comparison may be used in detection of the difference in equilibrated and nonequilibrated gases passing by the sensors.

This invention can be used when operating the engine under closed-loop control, first with one sensor of a pair in the feedback control, and then the other during a short monitoring period, i.e., less than 20 seconds; a change in the feedback signal is observed to obtain a determination of catalyst degradation. The change from one sensor to the other may be cyclically controlled at a repeating frequency to enhance reliability of the system. A correlation is made between resulting changes in the signal with switching frequency.

Another aspect of this invention is the construction of a single sensor body having dual electrodes, one electrode being highly catalytic and the other being low-to-noncatalytic. The construction may have a common solid electrolyte zoned for two sensors by use of a barrier and two pairs of platinum electrodes, one of the pairs being exposed to an air reference cell and the other pair exposed to exhaust gases. One pair has the exhaust exposed electrode highly catalytic by use of a thin overcoating of porous platinum, and the other pair has the exhaust exposed electrode devoid of such coating or deactivated by lead or silver to produce a low-to-noncatalytic electrode. To simplify and make less expensive, the air reference may be eliminated from the construction and the differentially catalyzed electrodes placed on opposite sides of a non-zoned electrolyte thereby immersing the entire device in the exhaust gas.

BRIEF DESCRIPTION OF THE DRAWINGS

FIG. 1 is a block diagram of the essential steps of the method of this invention.

FIG. 16 is a composite schematic view of two oxygen sensor constructions, one with a highly catalyzed electrode exposed to exhaust gases, and the other a low-to-noncatalyzed electrode so exposed.

FIG. 19 is a view similar to FIG. 17, but showing still yet another sensor construction.

DETAILED DESCRIPTION AND BEST MODE

Figure 2:
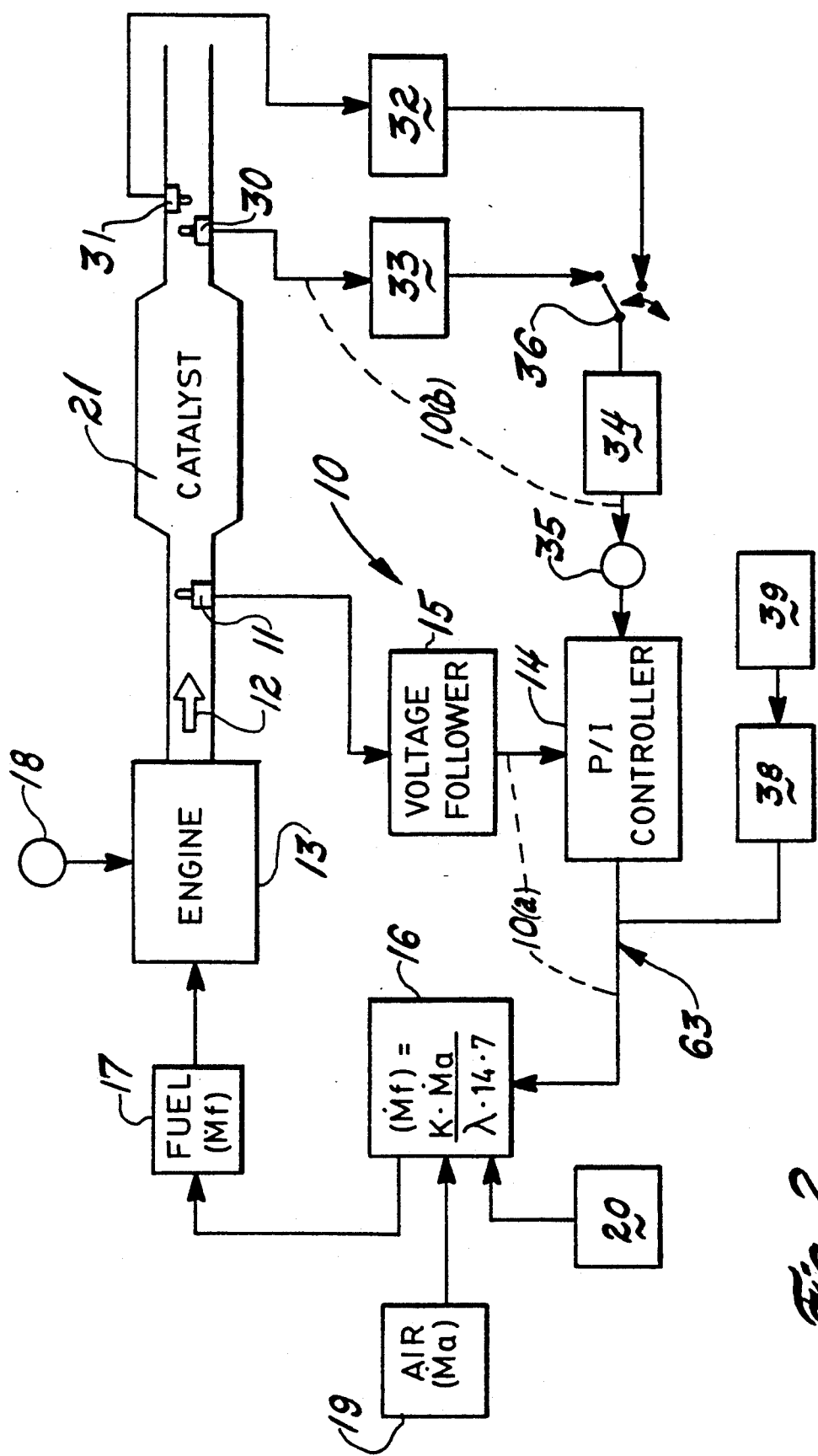
FIG. 2 is a schematic illustration of one usage of sensors of this invention with electrodes having significantly different catalytic activity, the usage here being for catalyst monitoring in a closed-loop feedback engine control having upstream and downstream control sensors (with respect to the catalyst) for feedback A/F control.

It is conventional wisdom in the art that an oxygen sensor will be able to detect a change in oxygen storage capacity of a catalyst and thereby presumably detect catalyst efficiency. Attempts to implement this wisdom have used a conventional oxygen sensor placed downstream of the main catalyst, but it also functions as a catalyst, more accurately a microcatalyst, because its electrode, exposed to the exhaust gases, is highly catalytic in accordance with conventional construction. It is theorized that when the main catalyst degrades, it cannot cyclically store oxygen. Thus, the EGO sensor will provide a switching signal increased in frequency and/or increased in amplitude. However, the actual signal must be compared to a reference signal or library of reference signals to judge whether the main catalyst is degraded. Matching reference signals properly may lead to erroneous results because of the variable instantaneous conditions within the system. Amplitude changes are unreliable as an indicator of catalyst degradation because such changes are caused by changes in the oxygen storage of the catalyst, not necessarily by changes in its conversion efficiency. Also, some change in sensor output could be caused by changes in the response of the sensor itself. Frequency change may not be an indicator of a degraded catalyst for the same reasons given above.

To avoid the need for reference signals, it has also been theorized that an artificial fuel pulse be used to exceed the storage capacity of the main catalyst; analysis of the sensed signal, before and after the pulse, tends to more clearly indicate a degraded catalyst without the need for reference signals. This approach may be difficult to implement because of the need to use the downstream sensor in a closed-loop engine control and maintain the exhaust gases within a desired window of air/fuel ratio optimum for main catalyst conversion efficiency.

The invention herein avoids any reliance on a correlation between oxygen storage of the main catalyst and its efficiency. In the preferred embodiment, two differentially catalyzed EGO sensor electrodes, whether integrated along one common electrolyte or used in separate electrolyte constructions, are substituted for the conventional EGO sensor downstream of the main catalyst; simultaneous and instantaneous comparison of the actual signals from each of such electrodes provides very reliable proof as to the efficiency of the main catalyst. Unreliable reference signals are avoided, the engine control system is not disrupted to accommodate catalyst monitoring, and false conclusions from reliance on the catalyst's ability to store oxygen is avoided.

Essentially, the method of this invention comprises two main steps. The first step is to expose differentially catalyzed electrodes of an oxygen sensing system to essentially the exhaust gases from an engine (both being either upstream or downstream of the main catalyst, designed to convert all of such exhaust gases). The second step compares the signal outputs from such electrodes for an indication of a specific malfunction with respect to engine misfire, combustion deficiency, or main catalyst degradation (see FIG. 1).

System Usage

A first aspect of this invention is concerned with how the differentially catalyzed sensor electrodes, exposed to the exhaust gases, are used in a catalyst monitoring system. As shown in FIG. 2, a closed-loop feedback control can be employed having a primary feedback loop 10(a) and an enhancement feedback loop 10(b). In the primary feedback loop, a conventional EGO sensor 11 is disposed in the emission flow 12 from an engine 13 (upstream of the catalyst), the signal from the EGO sensor 11 being connected to a feedback controller 14 which in turn supplies control information to an on-board computer or base fuel calculation means 16. Means 16 transmits a command signal to a fuel injector driver 17, the command signal controlling the pulse-width converter of the injector driver. There may be several injector drivers to accommodate each of the combustion cylinders of the engine, each of which must receive fuel pulses to carry out combustion therein within the engine in combination with inlet air 18 supplied to the engine. The signal from the first EGO sensor 11 may be modified by voltage follower (comparator) 15 which reshapes the signal from a sine-like wave to essentially a square wave thereby alleviating the very high impedance of the sensor output. To enhance the feedback control loop, it may further contain adaptive tables 20 to provide more precise calculation of A/F ratios during dynamic conditions where the feedback system cannot respond rapidly enough. The on-board computer or fuel calculation means 16 also receives information of mass airflow from a device 19. The controller 14 is preferably a proportional-integral type wherein the coefficients of proportional-integral terms of a control algorithm are adjusted to a different gain. Gain is the slope of the signal output to the signal input (essentially its strength). The gain of the signal directly from the sensor is extremely high at the switch point and thus would lead to erratic adjustments if such signal was not modified with respect to its gain.

To provide for enhanced feedback control and catalyst monitoring, the secondary control loop 10(b) deploys a second EGO sensor 30, having a highly catalytic electrode 30(a) exposed to the exhaust gases, and a third EGO sensor 31, having a low-to-noncatalytic electrode 31(a) exposed to the exhaust gases; sensors 30 and 31 are arranged for alternate connections to the feedback controller 14. The second and third EGO sensor electrodes that are exposed to the exhaust gases may be combined as a single split sensor construction placed after the catalyst to perform the monitoring. Such a split EGO sensor would actually be two EGO sensors in one; one of the EGO sensors would have a highly catalytic coating and the other would have no or little catalytic coating.

Each signal from the second and third sensor electrodes 30(a) and 31(a) are respectively modified by a separate voltage follower or comparator 32, 33. The voltage follower is useful because the signal emanating from the sensor itself has very high impedance. The signal from the follower is then subjected to a low-gain modifier 34 or integrator. Thus, the signal is developed at an output that increases with time at a constant rate or that decreases at a constant rate to vary the pulse width of the air/fuel ratio controller in a closed-loop manner. The low-gain modifier switches from an increasing ramp to its decreasing ramp and back again in response to the output of the follower or comparator, which can be either one of two levels. The comparator changes or switches levels at a point where the waveform voltage of an oxygen sensor exceeds a reference voltage input to the comparator. The reference voltage input to the comparator is preferably known to be a voltage that will provide a uniform result even in conditions where the sensor waveform ages.

The signal may further be modified by a bias adjust 35. The bias adjust is useful to compensate for dislocation of the air/fuel ratio signal to the lean side due to a slow change of partial pressure of oxygen, even when at the stoichiometric point of the sensor. This bias adjust moves the air/fuel ratio back to the proper window.

The enhanced feedback system uses the highly catalytic electrode 30(a) (or second sensor) in normal mode to provide the enhanced feedback control. The low-to-noncatalytic electrode 31(a) (or third sensor) is alternately switched into the enhanced feedback system control and a comparison is made between the signals from such differentially catalyzed electrode(s) (sensors). A switch 36 is interposed into the enhanced feedback loop preferably after the comparators 32, 33. Although the switch 36 may be disposed at other locations in the signal connection between the sensors and the controller, it is desirable at this location because it minimizes the use of redundant components. Comparison may be carried out by use of a detector 38 connected to the signal output of the controller 14 (sensing the A/F signal-LAMBSE) which in turn is interpreted by an indicator block 39 to alert the driver to the desired malfunction of the catalyst. Comparison of the signal output from the controller is advantageous because it allows a more accurate determination of the degree of degradation of the catalyst as will be discussed later.

Figure 3:
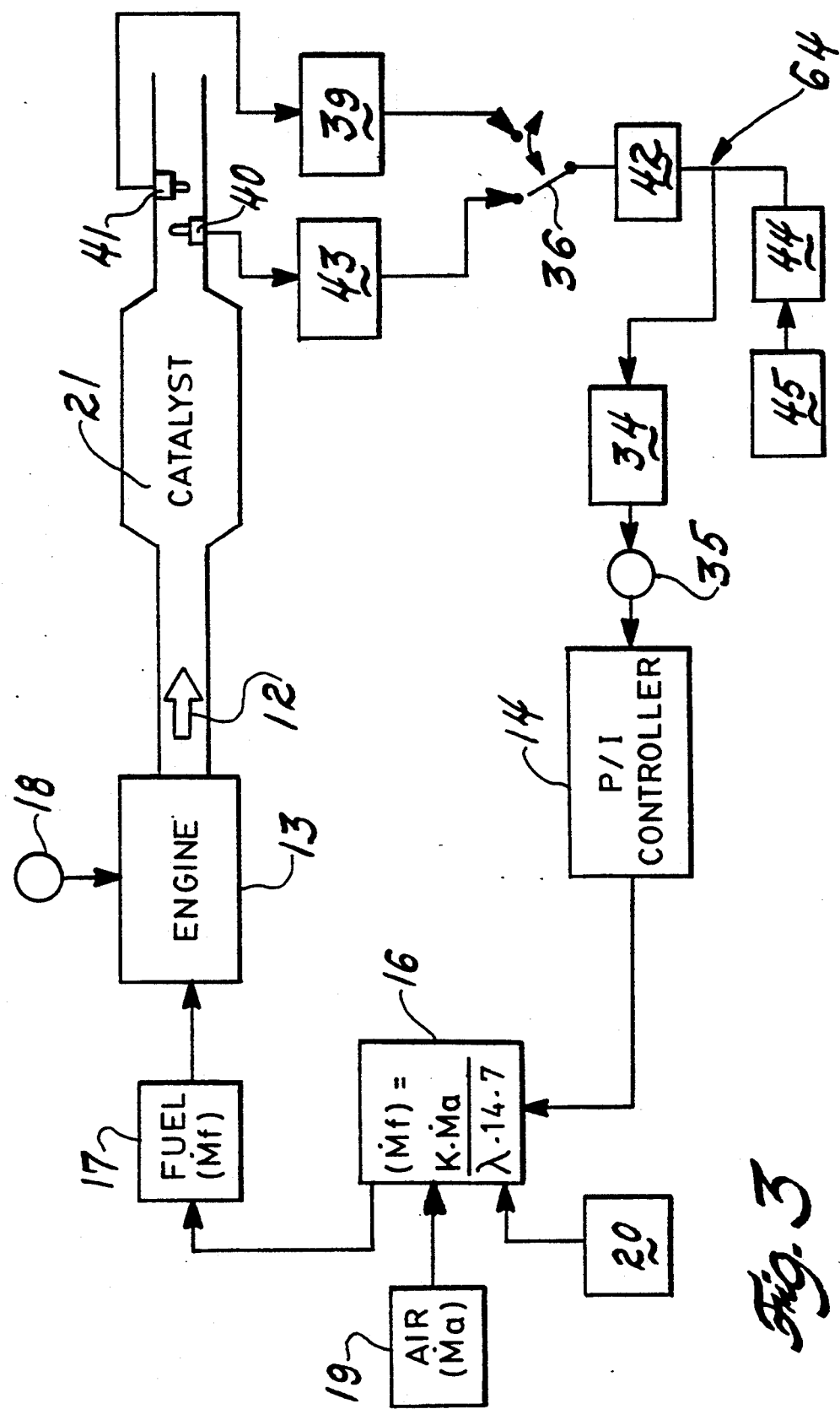
FIG. 3 is a schematic illustration of another usage of sensors w electrodes having differing catalytic activity but using only the downstream highly catalytic electrode sensor for feedback A/F control while the pair provides catalyst monitoring.

Alternate usage schemes for the differentially catalyzed electrodes of an oxygen sensor are shown in FIGS. 3-6. In FIG. 3, the use of an upstream sensor to provide primary feedback control is eliminated (either during the detection test or during all engine operations). The highly catalytic electrode 40 of the downstream split sensor (or pair of sensors) may be used as the normal mode for feedback A/F control and the low-to-noncatalytic electrode 41 is used only during catalyst interrogation. It may be desirable to cyclically switch back and forth between the highly catalyzed and noncatalyzed sensor electrodes at some suitable frequency (rather than just switching once); the resulting changes in the feedback A/F signal are correlated with the switching signal frequency. This can be done by use of a repeater device 42 which promotes the cyclical switching. Such switching is done in order to obtain a catalyst monitoring signal that alternates between two values (during the catalyst testing interval) rather than a signal which just switches once. The potential advantage in doing this is that the procedure may provide more reliability in identifying marginally defective catalysts. The cyclical switching operation would only be performed during a designated catalyst monitoring interval such as for about 20 seconds. When the catalyst monitoring is not being performed, the highly catalyzed electrode or sensor 40 (rather than the low-to-noncatalyzed electrode or sensor 41) would be used in the feedback A/F control or feedback trimming enhancement to provide the maximum air/fuel control accuracy. The other elements modifying the A/F control signal may be the same as in FIG. 2 or simplified as shown in FIG. 3. Detection of a signal difference is here made prior to the low gain adjust 34 and bias adjust 35. Detection is by way of block 44 (which simply compares the difference between output from sensors 40 and 41 and produces a malfunction indication signal to malfunction indicator 45 when the difference is greater than a preset value corresponding to a bad catalyst. Preset value could be a function of speed and torque.

Figure 4:
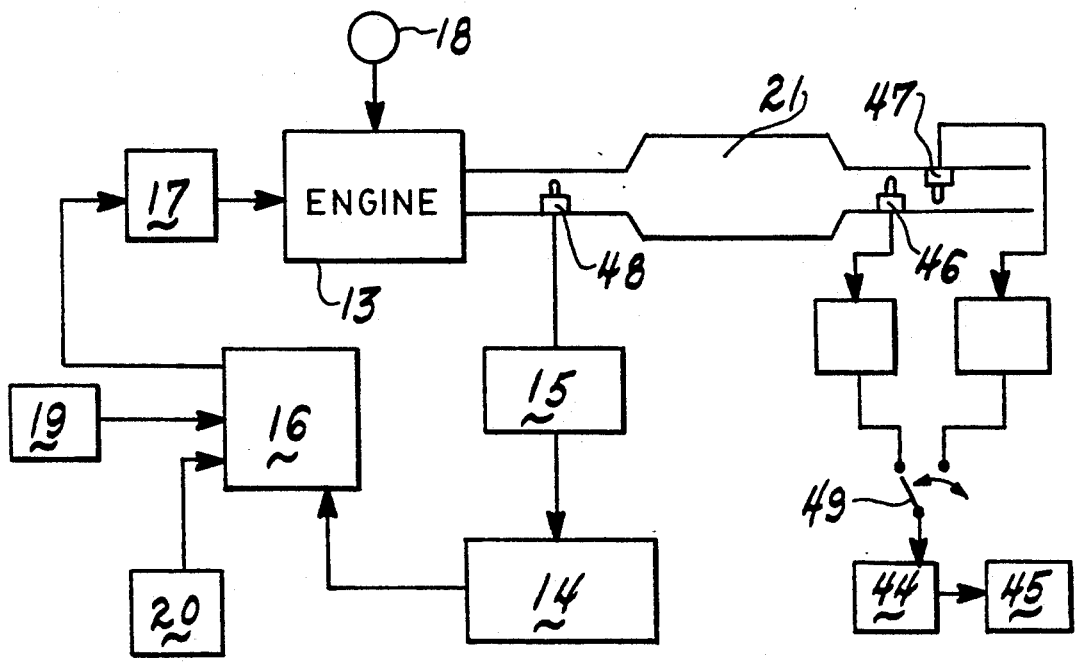
FIG. 4 is an alternative system like that in FIG. 3, but using the downstream sensor pair in open loop while using an independent upstream sensor for feedback A/F control.

As shown in FIG. 4, differentially catalyzed electrodes (or sensors) 46 and 47 may be placed downstream of the catalyst in open loop, with upstream sensor 48 operating in closed loop to feed back oxygen sensing information for A/F control. A switching device 49 may be cyclically controlled by repeater as shown. Detection and indication of malfunction is made similar to FIG. 3.

The broad concept of this invention does not depend on which type of combusting device is upstream of the differentially catalyzed electrodes (sensors). The concept can be used to detect misfire and slow or late burn of each of the cylinders contributing to improper engine combustion, which improper combustion may damage the main catalytic converter. Two sensors or one split sensor device can be located upstream of the main catalyst converter 21 but downstream of the engine exhaust manifold of the engine 13. One EGO sensor (having only one type of catalyzed electrode), regardless of position in the exhaust stream, cannot readily detect improper combustion. But, differentially catalyzed sensors (electrodes) of this invention can do so readily. It has been discovered that the low-to-noncatalyzed sensor (electrode) will exhibit a decided change in frequency when there is an ignition misfire (that is to say, the noncatalyzed sensor will produce an output signal having high frequency components corresponding to the rate of the misfire); a low-to-noncatalyzed sensor (electrode) will also exhibit a change in amplitude when slow or late cylinder burn occurs.

Figure 5:
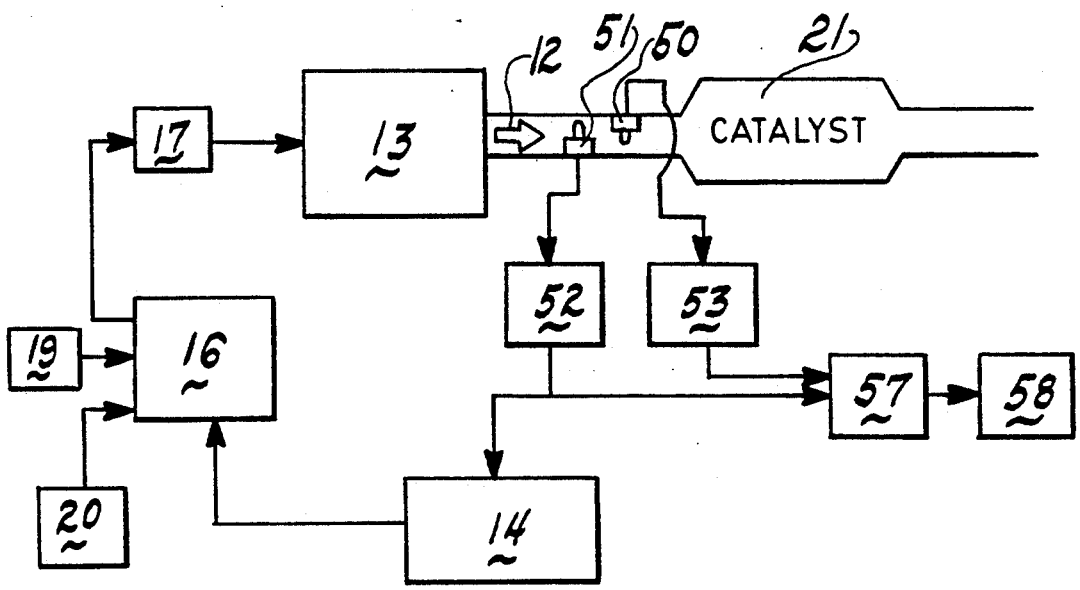
FIG. 5 is still another usage of sensors with electrodes having different catalytic activity but using the upstream highly catalyzed electrode sensor for feedback A/F control while the pair provides engine misfire or slow or late burn detection.

As shown in FIG. 5, sensor 50, having a highly catalytic electrode, and sensor 51, having a low-to-noncatalytic electrode, are placed downstream of engine 13 but upstream of catalyst 21. The sensor 50 is normally connected in closed-loop feedback A/F control of the engine. The signal from each of the sensors is fed to a detection block 52 which is effective in determining when there is a sufficient difference in frequency or amplitude to alert a malfunction indicator 53 of misfire or slow or late burn.

Figure 6:
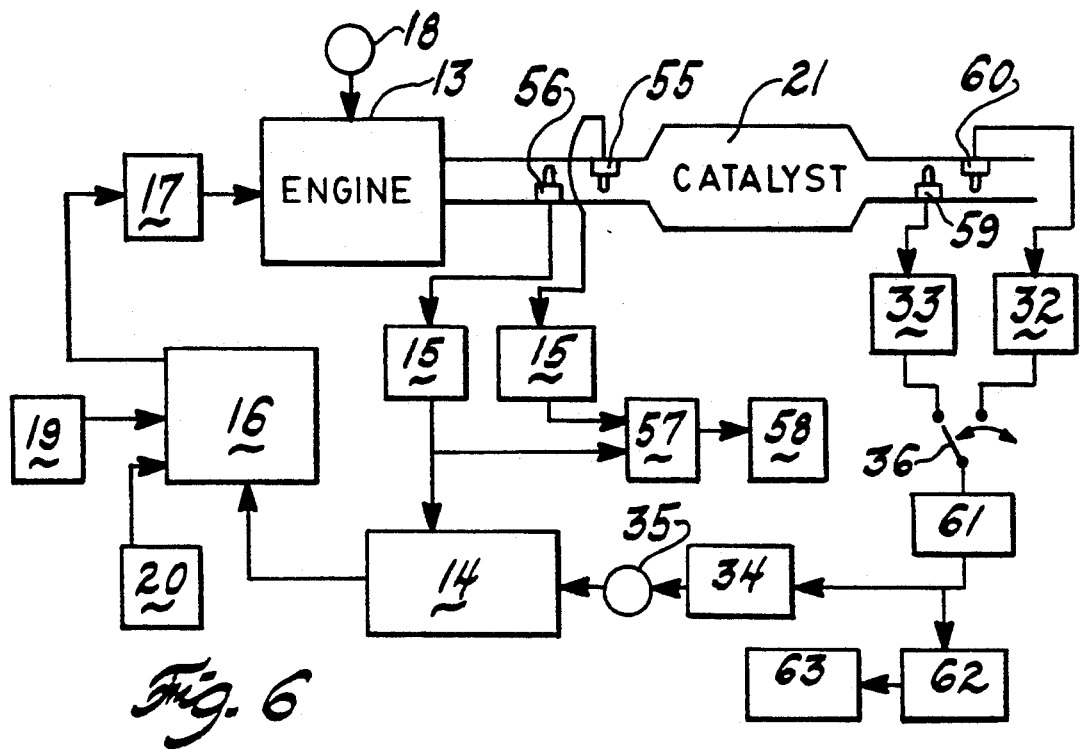
FIG. 6 is a schematic illustration of yet still another usage of sensors with electrodes having differing catalytic activity, the usage here being for monitoring both engine misfire/combustion malfunction and catalyst degradation by the use of two pairs of sensors.

The use of differentially catalyzed sensors (electrodes) may be used to detect both misfire and combustion malfunction as well as provide interrogation of the main catalyst for proper functioning (see FIG. 6). In this embodiment, the highly catalyzed electrode (sensor) 55 acts to provide the normal oxygen sensing for closed-loop feedback A/F control. The low-to-noncatalyzed sensor (electrode) 56 is continuously compared by way of a detecting block 57 to trigger a malfunction indicator 58 if justified.

The downstream differentially catalyzed sensors (electrodes) 59 and 60 are used the same as in the embodiment of FIG. 2 to periodically interrogate the main catalyst 21 as to its efficiency. A repeater device 1 may be utilized to switch between each of the sensors (electrodes) 59 and 60 to make the comparison. Detector 62 and malfunction indicator 63 receive and operate on the signal received upstream of low gain block 34 and bias adjust 35.

Comparing Signals

This invention uses differentially catalyzed electrodes (sensors) that allow the monitoring system to be specific to combustion (whether performed by the engine or by the catalyst) while eliminating temperature and flow sensitivity and eliminating the distortion and interference inherent in absolute measurement from a single device.

Figure 7:
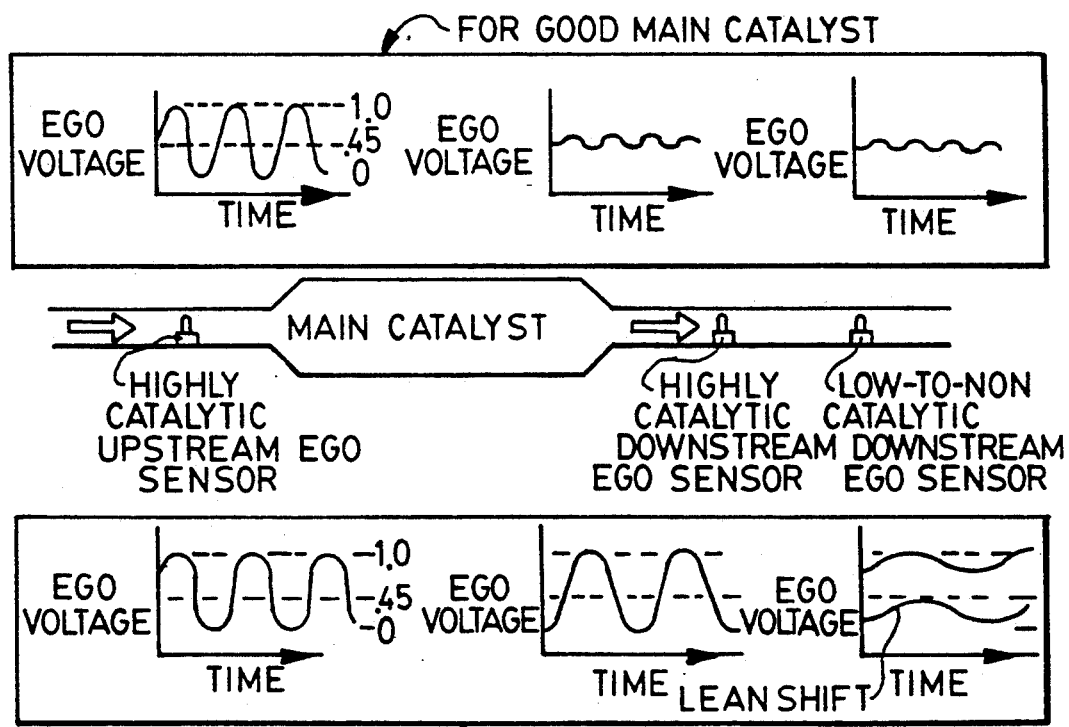
FIG. 7 is a composite of graphical illustrations of EGO signal voltage as a function of time, the first row of views respectively are for a highly catalytic electrode exposed to upstream exhaust gases, a highly catalytic sensor exposed to downstream exhaust gases, and a low-to-noncatalytic electrode exposed to downstream exhaust gases; the upper boxed group of signal views illustrating the effect of a good main catalyst and the lower boxed group of signal views illustrate the effect of a bad main catalyst.

For catalytic monitoring, a standard oxygen sensor with a highly catalytic electrode exposed to the exhaust flow downstream of a main catalyst can exhibit a voltage signal that shows little change from the signal sensed by an upstream sensor with a highly catalytic electrode when the main catalyst is bad (see FIG. 7). Each sensor is seeing essentially the same type of unconverted exhaust gas and each sensor equilibrates such gas in essentially the same way. However, when the catalyst is good, there is a substantial difference in signal between the highly catalytic upstream and downstream sensors. This substantial change in signal may be attributed to the fact that a good main catalyst fully equilibrates the exhaust gases prior to the downstream sensor seeing such gases. However there is a decided change in signal in the downstream sensor, when highly catalytic, depending on whether the main catalyst is good or bad.

Figure 8:
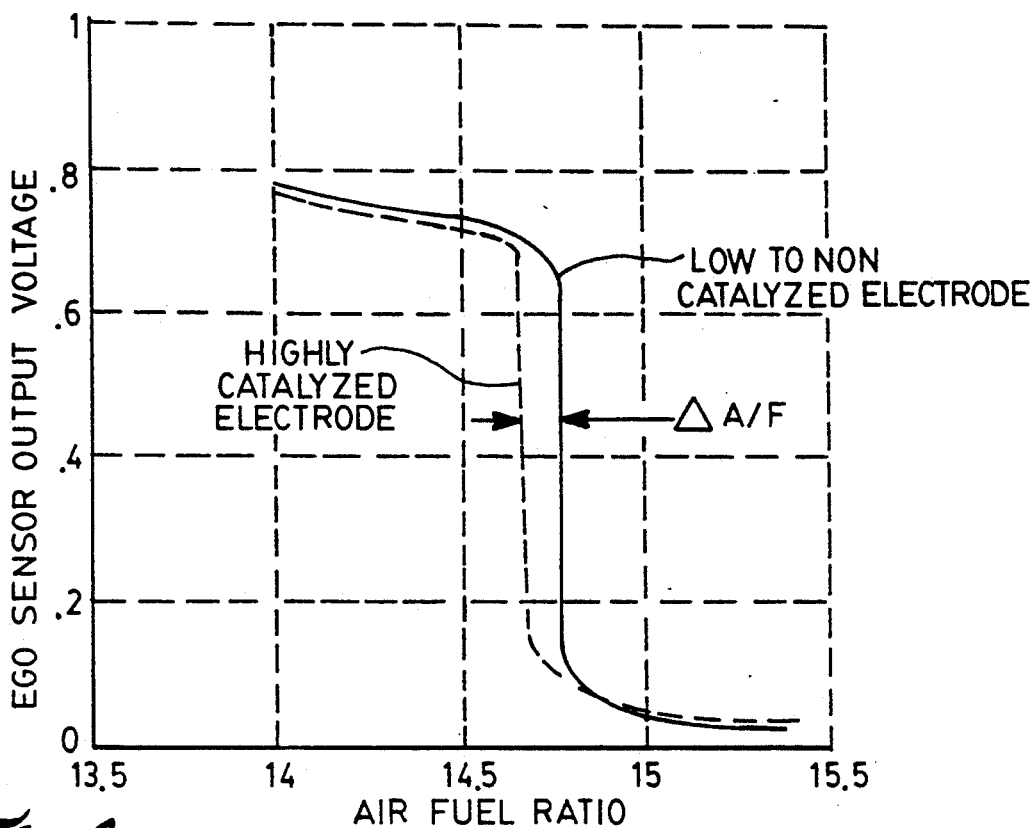
FIG. 8 is a graphical illustration of oxygen sensor voltage plotted as a function of A/F signal.
Figure 9:
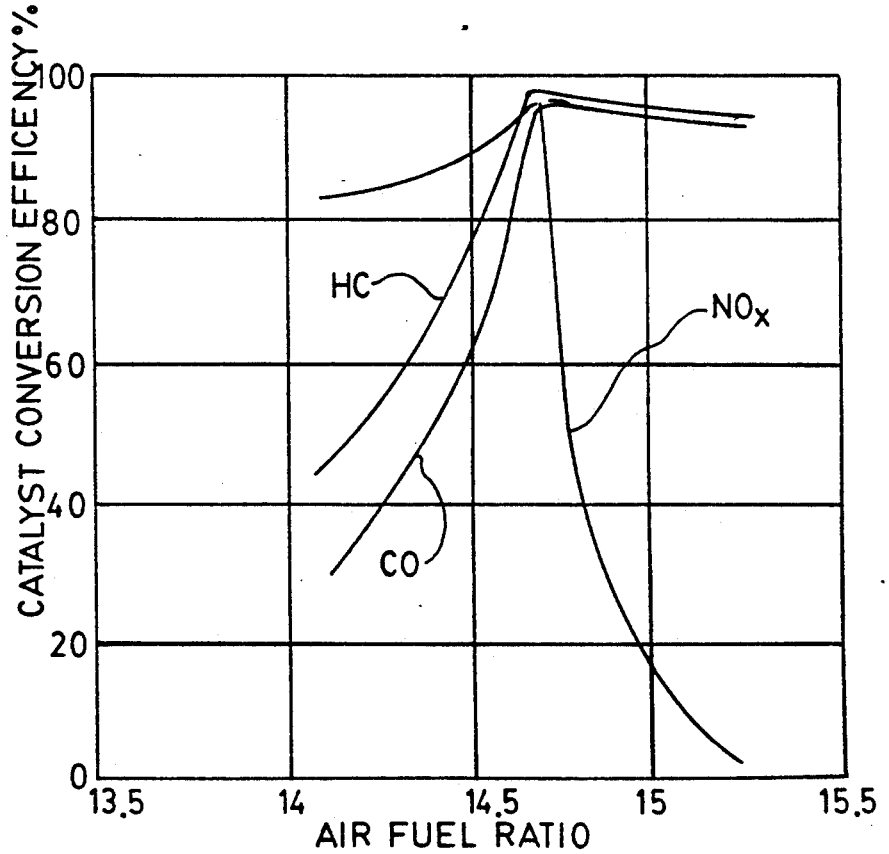
FIG. 9 is a graphical illustration of main catalyst conversion efficiency plotted as a function of A/F signal.
Figure 10:
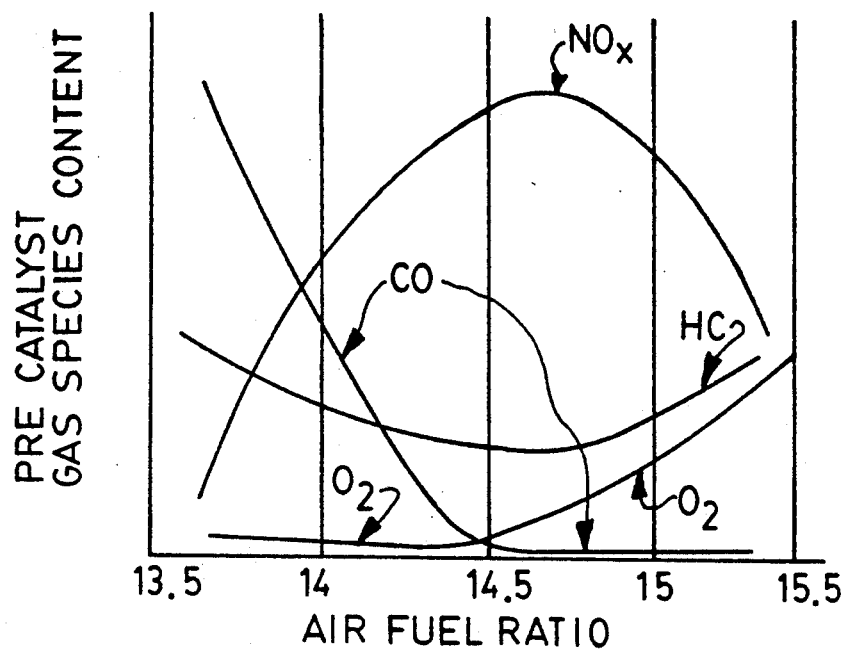
FIG. 10 is a graphical illustration of pre-catalyst gas species content plotted as a function of A/F signal.

Even more clear is the fact that a highly catalyzed sensor (electrode) characteristic is shifted rich compared to the noncatalyzed sensor (electrode) (see FIG. 8). A rich shift herein means that the catalytic sensor will produce a certain mid-range output voltage at an A/F ratio which is richer than the A/F ratio required for the noncatalytic sensor to produce the same output voltage. The amount of A/F shift is dependent on the catalytic activity (i.e., on the conversion efficiency) of the main catalyst. A goal of this invention is to be able to operate the engine under closed-loop control with first one sensor in the feedback control and then the other in the feedback control and observe the change in the engine A/F feedback signal (LAMBSE) while doing so. Since the two sensors will produce the same output voltage at a different A/F value, there will be a difference in the A/F feedback signal of the engine depending on which sensor is in control (see FIG. 9). The reason there is a shift in the A/F, depending on whether the catalyzed or low-to-noncatalyzed electrode is used, can best be understood by reference to FIG. 10. But a low-to-noncatalytic sensor, placed downstream of the main catalyst, will exhibit little amplitude change in signal between a good and bad catalyst. The exhaust gases are passing through the main catalyst equilibrated in the case of a good catalyst but essentially unconverted in the case of a bad catalyst. But since the sensor cannot itself equilibrate the gases, there is a saturation of the sensor and the signal appears as a stretched form of the good catalyst signal, possibly at different levels due to a different mean A/F of the modulating A/F signal. Thus, when a sensor is capable of equilibrating itself, it will exhibit a greater signal amplitude and/or frequency. Therefore, since the difference between the two sensor characteristics is a function of the catalyst conversion efficiency, the magnitude of the change in the A/F feedback signal (LAMBSE), which occurs when switching from one sensor to the other, can be used as an indicator of the catalyst condition.

Although this invention comprehends detecting the signal of the differentially catalyzed electrodes (sensors) anywhere along the closed-loop circuit, it is preferred to detect the A/F ratio feedback signal (LAMBSE). This preference can be understood by reference to FIGS. 12 and 13.

Figure 11:
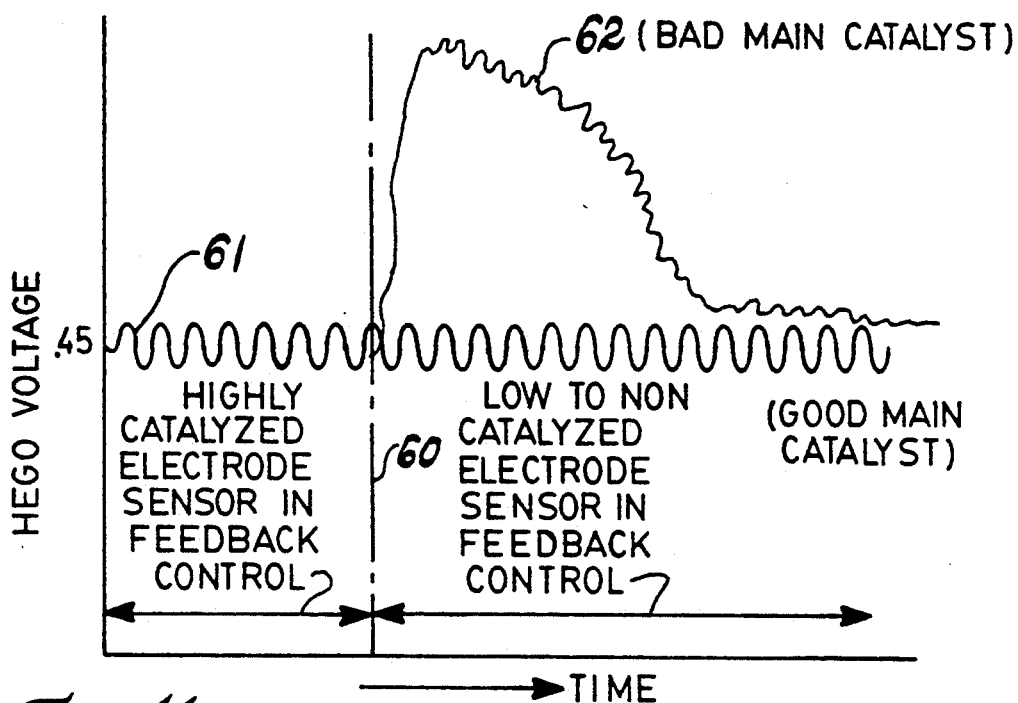
FIG. 11 is a plot of voltage signal taken prior to the P-I controller, such signal being plotted as a function of time for both a highly catalyzed electrode and a low-to-noncatalyzed electrode exposed to both a good and bad catalyst.

During use of the highly catalyzed sensor (electrode), shown to the left of line 60 in FIG. 11, the voltage signal is relatively steady at a predetermined plateau 61. When the low-to-noncatalyzed electrode (sensor) is made operative by switching, the voltage signal (to the right of line 60) will exhibit a difference if the main catalyst is bad. The voltage will abruptly rise to a new plateau 62 and gradually recede to its original plateau as the A/F controller readjusts the A/F ratio. To see a decided difference in signal, using the voltage data of FIG. 11, the comparison must be made rather quickly at a moment when the voltage has made a sharp move, which leads to inaccuracy because of its rapid change. If the comparison is made too slowly, i e., about 10–15 seconds, the voltage will have receded and little difference will remain. Furthermore, the plateau 62 will saturate at some limiting value for all catalysts having conversion efficiency below a certain value.

Figure 12:
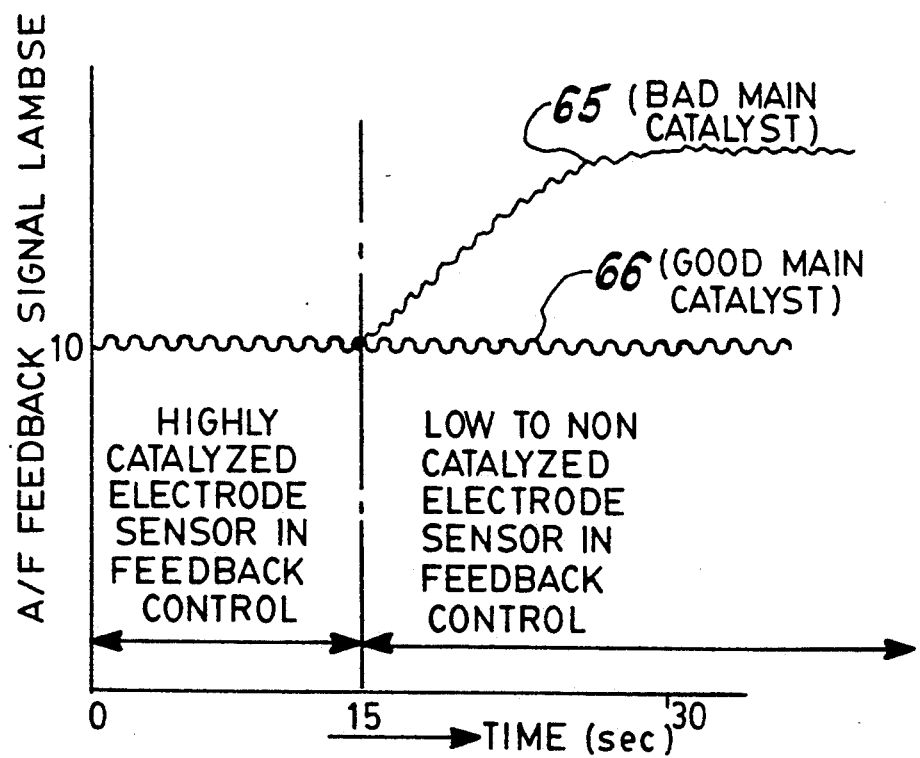
FIG. 12 is a plot of A/F signal as a function of time for both a highly catalyzed electrode and for a low-to-noncatalyzed electrode.

In FIG. 12, a preferred signal comparison is illustrated. The A/F feedback signal is sensed This may be accomplished by taking the signal at a location 63 (A/F feedback signal), as shown in FIG. 2, as opposed to taking the voltage signal at a location 64, as shown in FIG. 3. As shown in FIG. 12, the feedback signal, using a low-to-noncatalyzed electrode, will gradually rise to a new plateau 65 over a period of 5–10 seconds if the main catalyst is bad. In the case of a good catalyst, the A/F feedback signal will remain substantially at the original plateau 66, essentially the same as for the highly catalyzed sensor (electrode). This enables an interrogation scheme whereby after about 5–10 seconds, from the time the highly catalyzed electrode is switched to the low-to-noncatalyzed electrode, a clear, definite signal comparison can be made, free from inaccuracies.

Figure 15:
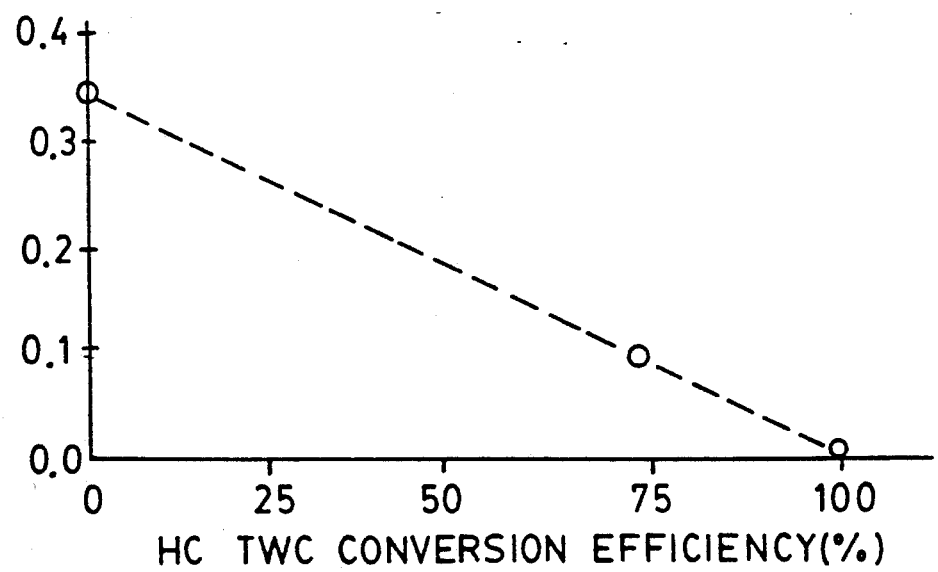
FIG. 15 is a graphical illustration of A/F shift as a function of catalyst conversion efficiency, the difference in A/F signal between catalyzed and noncatalyzed sensors placed downstream of three catalysts, of known but varied catalyst efficiency, was plotted.

An additional virtue of using the A/F feedback signal for detection (i.e., taken at 63) is that it permits determination of a degree of malfunction or efficiency. The amount of A/F shift (or Δ A/F) is indicative of the degree of hydrocarbon conversion efficiency degradation of the main catalyst. Engine/dynamometer tests were performed using the system of FIG. 2. Specifically, closed-loop A/F measurements were made with first the highly catalytic sensor and then the noncatalytic EGO sensor in control, and the differences between the closed-loop A/F for each situation was determined The tests were repeated using three different catalysts and the results were plotted as a function of hydrocarbon conversion efficiency as shown in FIG. 15. Examination of the results shown in FIG. 15 verify that the invention concept works as anticipated for the catalysts examined.

However, when using the voltage signal, such as taken-at location 64, the amplitude or frequency gives no clue as to the degree of efficiency of the catalyst.

Figure 13:
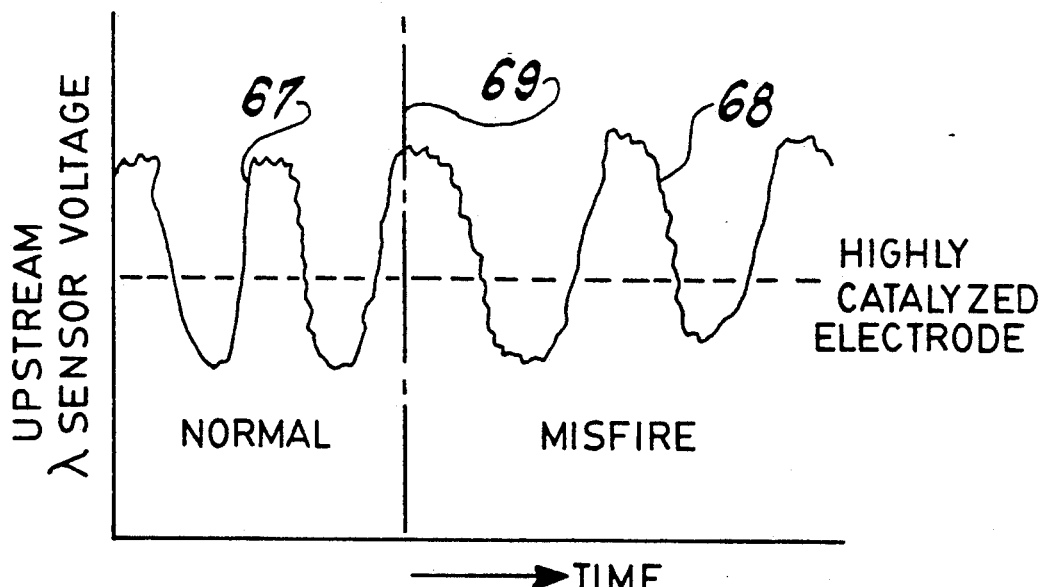
FIGS. 13 and 14 are respectively plots of (LAMBSE) voltage signal as a function of time for a highly catalyzed electrode and for a low-to-noncatalyzed electrode, the plots being marked to show when a misfire intentionally occurred.
Figure 14:
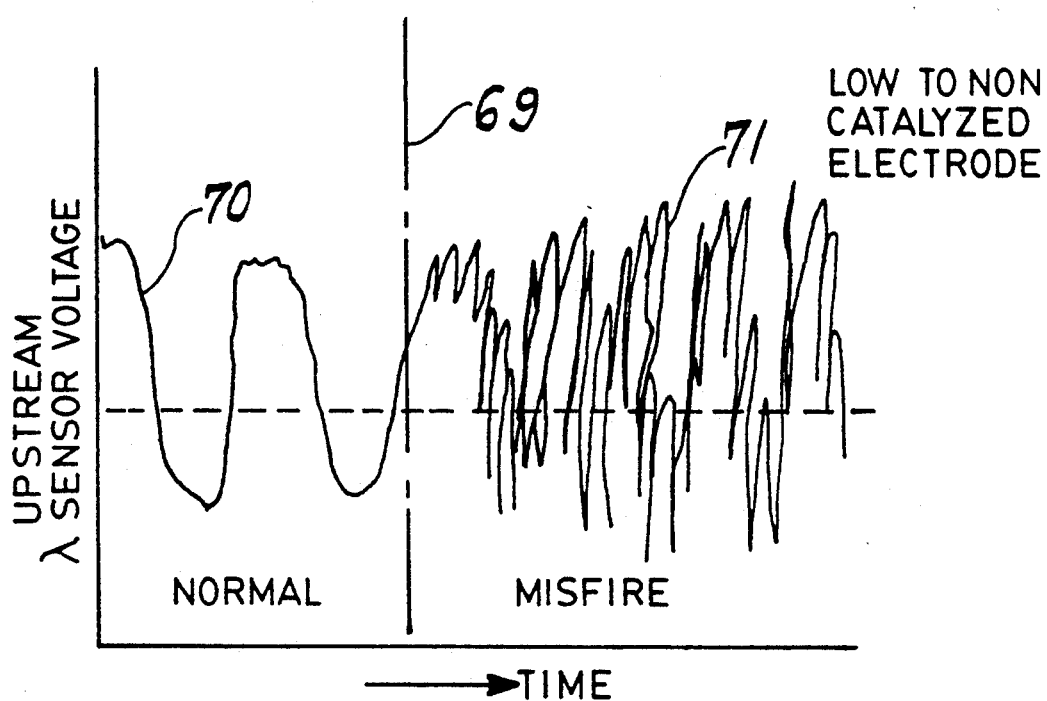

The voltage signal obtained from the sensor when placed upstream and used to detect misfire of combustion malfunction, is illustrated in FIGS. 13 and 14. A highly catalyzed electrode (sensor), as shown in FIG. 13, will exhibit a voltage variation that is roughly sinusoidal (for normal limit cycle operation) for both signals 67 and 68 during normal combustion and cylinder misfire conditions, respectively. However, when the low-to-noncatalyzed electrode (sensor) is activated, the voltage variation 70, 71 differs significantly from the normal combustion (to the left of line 69) and cylinder misfire (to the right of line 69) as shown in FIG. 15. The frequency is highly increased when a misfire occurs. Slow or late burn (other combustion malfunctions) will give rise to an amplitude change in the voltage signal of the low-to-noncatalyzed sensor (electrode).

Sensor Construction

FIG. 16 shows a consolidated view of both a highly catalyzed sensor construction on the top side 16(a), and at the bottom side 16(b), a sensor construction having a low-to-noncatalyzed electrode exposed to the exhaust gases. The construction of FIG. 16(a) has a thimble-like structure positioned in the exhaust system of the engine. The exhaust gases 70 from the manifold, including unburned hydrocarbons, oxides of nitrogen, and carbon, along with $O_2$, are passed in Proximity to the oxygen sensor. The oxygen sensor 79 has a reference port 71 located within an insulator base 72 that receives ambient atmospheric gases comprised essentially of 79% nitrogen and 21% oxygen in the form of $O_2$. The oxygen sensor 79 further comprises a solid electrolyte oxygen ion conductor 73 of $ZrO_2$ or the like which has an inner electrode 74 of some noble metal, preferably platinum. On the outer surface of the solid electrolyte 73 is a highly catalytic electrode 75 comprised preferably of a noble metal solid strip, such as platinum, with a painted dot of porous platinum 75(a). A protective oxide covering 76, in the preferred form of a porous coating of $MgO \cdot Al_2O_3$ spinel, overlays the entire outside active surface of the sensor 70. All the layers 73/74/75/76 are porous either to molecules or ions of oxygen; the two platinum conduction layers 74/75 and terminals 77/78 are interconnected thereto for the collection of electron current respectively.

Theoretically, the operation of such oxygen sensors occur by $O_2$ molecules becoming oxygen ions with the addition of four electrons at the surface of electrode 74. The oxygen ions then diffuse into the solid electrolyte 73. Since the partial pressure of oxygen is higher on surface 74 than on surface 76, the net oxygen ions will move freely through the solid electrolyte to the outer catalytic electrode 75. At this point, the oxygen ions will give up electrons and combine to form $O_2$ molecules once more. A net voltage will thus develop between electrode 74 and electrode 75 in response to the difference of partial pressure of $O_2$ between the exhaust gas and the ambient atmosphere. Increasing the difference in partial pressures between the electrodes will, as a rule, increase the voltage created. Generally, a net partial pressure of $O_2$ in the exhaust gas of about $10^{-22}$ atmospheres (corresponding to rich A/F mixtures) will cause the sensor to output a voltage in the order of 1.0 volts. When the net pressure of oxygen increases, the sensor output voltage decreases, becoming less than 0.1–0.2 volts when the new partial pressure of $O_2$ in the exhaust gas is $10^{-2}$ atmospheres or more (corresponding to lean A/F mixtures).

It has been discovered that a sensor without the thin platinum overlayer 75(a), equivalent to the structure in FIG. 16(b), cannot equilibrate the exhaust gas behind a bad three-way catalyst; the sensor is essentially a low-to-noncatalytic electrode sensor. Such construction merely has an outer platinum electrode 99 in the form of a long, thick platinum strip but absent a thin porous platinum overlayer. It is the platinum overlayer that promotes the high catalytic activity.

Figure 17:
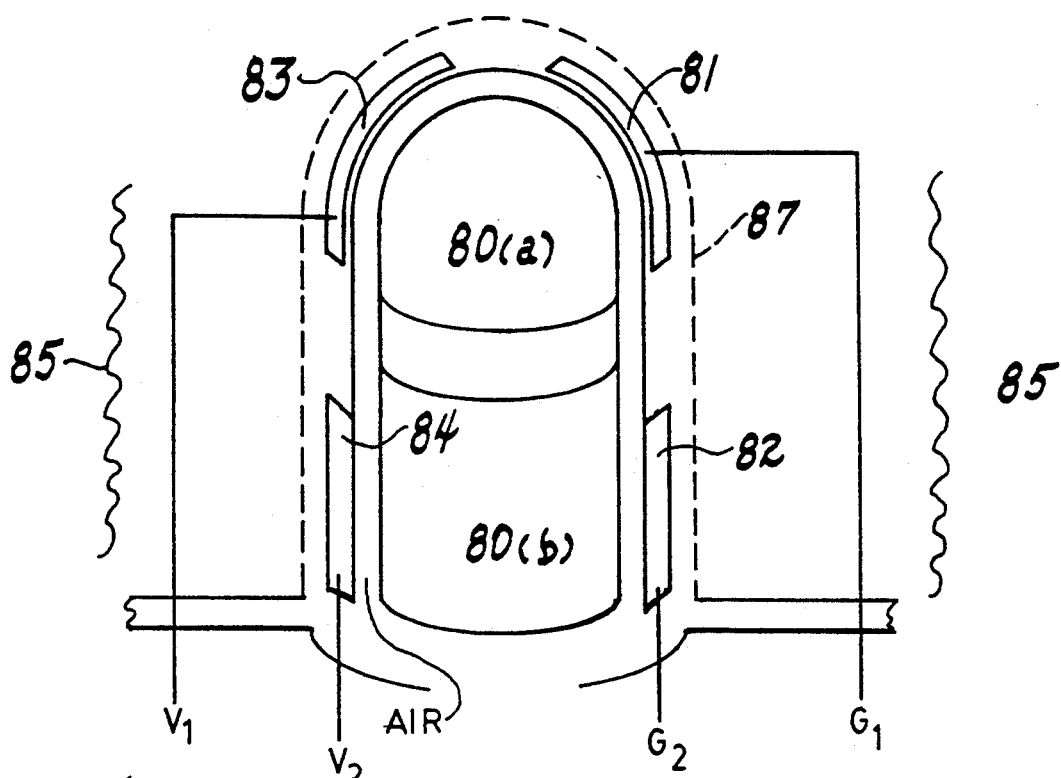
FIG. 17 is a schematic view of an integrated oxygen sensor construction that provides essentially two separate oxygen sensors in one device, one being highly catalytic and the other not.

An integrated closed-loop sensor construction is shown in FIG. 17 as an improved and alternative embodiment. Using two separate EGO sensors to implement the method of this invention, differences might arise due to sensor location, local flow, different heater temperature, etc. These differences could be minimized by carefully engineering, but are largely eliminated by constructing the two sensors on a single substrate as shown in FIG. 17. This will enhance the accuracy of the monitoring over that performed using two sensors. The proposed device of FIG. 17 incorporates two oxygen sensors on a single oxygen conductive substrate 80. Both devices would then be subjected to nearly identical location, flow, temperature, and aging conditions to lower output differences because of these interfering factors. The electrolyte is separated into two portions 80(a) and 80(b) by a material to prevent cross-talk ($O_2$ transfer between two sensors). Alumina ($Al_2O_3$) may be used as such insulating material 87. The portion of the sensor which would carry out highly catalyzed equilibration has an electrode 81 formed of a thin platinum strip accompanied by a highly catalytic overcoating of the electrolyte. To complete one part of the dual sensor, an electrode 83 is formed either of highly catalytic or noncatalytic material subjected to the air reference interior of the construction. On the other side of the construction is a low-to-noncatalyzed electrode 82 which is exposed to the exhaust gases and accompanied by its other electrode 84 subjected to the air reference side, which electrode may be either catalyzed or non-catalyzed. To improve the accuracy of the device, a heating element 85 may be disposed to maintain the air reference temperature at an elevated level. Leads are connected to each of the electrodes as shown in FIG. 17 and respectively are labeled G1, V1, G2, and V2. Both air reference side electrodes could be of identical material. Both devices would be mounted inside a housing containing a heater, although this might not be essential in the case of devices used for catalyst monitoring only.

The insulating layer 87 ($Al_2O_3$) can be eliminated if the alternative construction of FIG. 19 is utilized. Electrodes 83 and 84 (of FIG. 17) are formed as a common inner electrode 88. The two differentially catalyzed electrodes (81, 82 of FIG. 17) are shifted laterally to become electrodes 86 89; cross-talk is minimized. This construction is desirable for mechanical reasons because $Al_2O_3$ can have a different thermal expansion coefficient than $ZrO_2$ (which can result in cracking).

Figure 18:
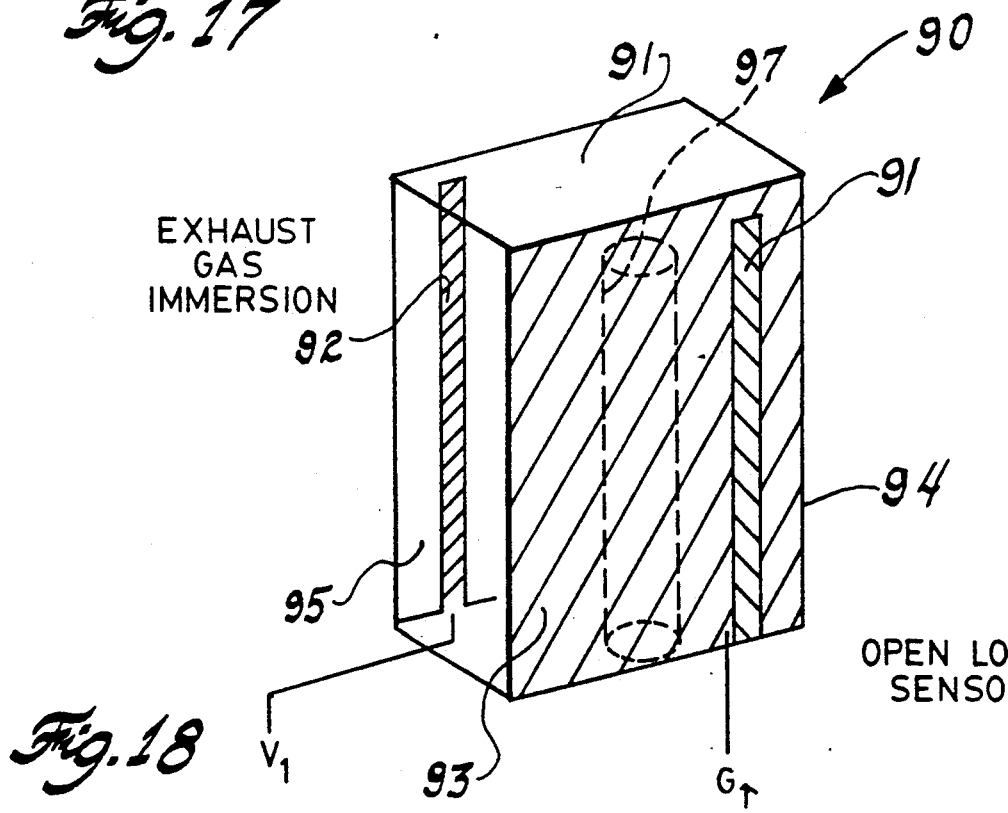
FIG. 18 is an oxygen sensor with differentially catalytic electrodes but having no air reference, both electrodes being exposed to the exhaust gases.

Still another alternative embodiment within the concept of this invention is a simplified open-loop type sensor 90 (as shown in FIG. 18) that eliminates the air reference and provides a differential measurement of the exhaust gas between a highly catalytic electrode 93 and a low-to-noncatalytic electrode 92. It consists of a single block or piece 91 of $ZrO_2$ electrolyte having one side 94 adapted to receive a highly catalyzed electrode by utilizing the conventional platinum strip/platinum overlayer combination, the overlayer providing the porous film that is necessary to provide the high catalytic activity. The opposite side 95 contains only a narrow, solid strip of platinum which operates low-to-noncatalytically. Alternatively, a thin silver layer may displace the solid platinum strip to operate as a noncatalytic electrode. The device is immersed completely in exhaust gases which makes the whole structure simpler and less expensive than a conventional EGO sensor. A central bored hole 97 completes the ability to immerse the entire electrolyte in exhaust gas. This type of sensor functions because the partial pressure between an equilibrated gas and a nonequilibrated gas promotes a difference in voltage. When the main catalyst is not functioning properly, this difference in voltage will be readily apparent However, when the main catalyst is operating properly, the difference in voltage will be relatively minor. Since this type of sensor will not operate as a switch type about stoichiometry, it cannot be used in a closed-loop fuel control system in addition to acting as a catalyst monitor.

We claim:

1. An exhaust gas oxygen sensor construction, comprising:
    (a) a solid electrolyte oxygen diffusion conductor divided to form separate electrically insulated portions, one side of both portions being exposed to ambient air and the other side of both portions being exposed to a common exhaust gas;
    (b) first and second electrodes on different portions of said electrolyte and each directed to an exposure of ambient air;
    (c) a highly catalytic third electrode on the electrolyte portion directed to an exposure of exhaust gas on which said first electrode is located and connected to said first electrode to provide a signal;
    (d) a low-to-noncatalytic fourth electrode on the other of said electrolyte portions directed also to an exposure of exhaust gas on which said second electrode is located and connected to said second electrode to provide another signal; and
    (e) means to discriminate a difference between said signals.

2. The construction as in claim 1, in which said oxygen diffusion conductor is (i) hollow, (ii) closed to form an air reference cell, and (iii) divided by a plane of nonconductive material.

3. The construction as in claim 2, in which said one side is the interior directed to ambient air and the other side is the exterior directed to exhaust gases, the exterior being protected by a porous coating of $MgO\cdot Al_2O_3$ spinel.

4. The construction as in claim 1, in which the first, second, and fourth electrodes are each a solid strip of noble catalytic metal, and the third electrode is a porous coating of noble catalytic metal.

5. The construction as in claim 1, which further comprises means for heating the sensor.

* * * * *